(12) United States Patent
Frank et al.

(10) Patent No.: US 10,383,536 B2
(45) Date of Patent: Aug. 20, 2019

(54) MEDICAL TUBULAR SHAFT INSTRUMENT

(71) Applicant: UNIVERSITY OF DUNDEE, Dundee (GB)

(72) Inventors: Timothy Graham Frank, Newport-on-Tay Fife (GB); Stuart Coleman, Dundee (GB)

(73) Assignee: University of Dundee, Dundee (GB)

( * ) Notice: Subject to any disclaimer, the term of this patent is extended or adjusted under 35 U.S.C. 154(b) by 1362 days.

(21) Appl. No.: 13/718,686

(22) Filed: Dec. 18, 2012

(65) Prior Publication Data
US 2013/0158526 A1    Jun. 20, 2013

(30) Foreign Application Priority Data
Dec. 20, 2011  (EP) .................................. 11194420

(51) Int. Cl.
*A61B 34/00* (2016.01)
*A61B 5/0404* (2006.01)

(52) U.S. Cl.
CPC ............ *A61B 5/0404* (2013.01); *A61B 34/70* (2016.02)

(58) Field of Classification Search
USPC .......................................................... 606/1
See application file for complete search history.

(56) References Cited

U.S. PATENT DOCUMENTS

| | | | |
|---|---|---|---|
| 6,500,189 B1 * | 12/2002 | Lang ................... | A61B 17/1611 606/170 |
| 6,817,974 B2 * | 11/2004 | Cooper ............ | A61B 17/00234 600/142 |
| 2002/0032371 A1 * | 3/2002 | Torii ..................... | A61B 1/0052 600/142 |
| 2007/0246507 A1 | 10/2007 | Sonnenschein et al. | |
| 2012/0143173 A1 * | 6/2012 | Steege ................... | A61B 17/29 606/1 |

FOREIGN PATENT DOCUMENTS

| | | |
|---|---|---|
| DE | 29512503 U1 | 9/1995 |
| DE | 20311293 U1 | 9/2003 |
| WO | 2004064600 A2 | 8/2004 |

* cited by examiner

*Primary Examiner* — Gary Jackson
*Assistant Examiner* — Jessandra F Hough
(74) *Attorney, Agent, or Firm* — Whitmyer IP Group LLC

(57) ABSTRACT

A medical instrument has a tubular shaft, a handle at a proximal end of the shaft and a movable working part at a distal end of the shaft, the shaft includes a shaft section having a curvature and being arranged between the distal end and the proximal end of the shaft. The handle and the working part are operatively connected via a force transmission element extending through the shaft. The force transmission element has a section arranged within the curved shaft section of the shaft, the section being guided on an inner surface of the shaft and having a plurality of interconnected single elements arranged one after the other along the longitudinal direction of the shaft. The single elements are pairwise connected by a pin forming a hinged joint, such that each of the pins defines a rotation axis oriented substantially perpendicular relative to the shaft.

14 Claims, 3 Drawing Sheets

MEDICAL TUBULAR SHAFT INSTRUMENT

BACKGROUND OF THE INVENTION

The invention relates to medical tubular shaft instruments of the type comprising a tubular shaft, a handle at a proximal end of the shaft and a movable working part at the distal end of the shaft. More specifically, the invention relates to medical tubular shaft instruments of the type comprising a shaft having a curvature between the distal end and the proximal end of the shaft, and the handle and the working part of which are operatively connected via a force transmission element extending through the shaft and being movable in a longitudinal direction of the shaft.

A medical tubular shaft instrument known from DE 203 11 293 U1 comprises a tubular flexible shaft at a proximal portion of which a handle is arranged. A distal portion of the tubular shaft is used to introduce jaws into a cavity of a patient during an operation for grasping and/or cutting tissue. The jaws are actuated by a force transmission element being accommodated within the flexible shaft and being movable along the longitudinal direction of the shaft. The force transmission element consists of a number of single segments being in contact with an inner surface of the shaft and being arranged next to each other along the shaft. The single segments are pairwise connected by ball joints.

The force transmission element of the known instrument is capable to transmit pushing forces. For transmitting pulling forces the known force transmission element has an additional flexible rod or cable extending through the single segments of the force transmission element.

The force transmission element of the known medical tubular shaft instrument has the drawback, that the ball joints connecting the single elements of the force transmission element only have pushing force transmission capabilities. Significant pulling forces can only be transmitted by the additional pull rod or cable which, however, increases the costs of the force transmission element. In addition, the assembling of the known medical instrument is exacerbated caused by the complex arrangement of the single segments and the pull rod or cable extending through the single element.

Furthermore, it is a disadvantage that the known force transmission element has poor torque transmission capabilities which are needed, if the jaws of the medical tubular instrument are rotatable about the longitudinal direction of the shaft.

It is easy to understand, that the single segments are not capable of transmitting significant torques from one segment to the other, since the ball head of one single segment which engages into the corresponding ball socket of a second single segment are in principle arbitrarily rotatable to each other about the longitudinal direction of the shaft. Beside this, the known ball joint connections can easily be affected by lateral forces leading to a deformation of the force transmission element which is known as buckling and/or flexing of these elements. These undesired effects typically occur by transmitting significant pushing forces along the axial direction of the force transmission element.

Another medical tubular shaft instrument is known from document DE 295 12 503 U1.

This known medical instrument has a curved shaft whose distal portion can be introduced into a body cavity of a patient. At the distal end of the curved shaft, jaws are arranged for cutting and/or grasping tissue during an operation. The jaws are actuated by a force transmission element being accommodated within the curved shaft and being movable along the longitudinal direction of the shaft. The force transmission element consists of a resiliently flexible material, wherein the diameter of the force transmission element is periodically decreased along the longitudinal direction of the force transmission element. The regions where the diameter is decreased and the regular regions form solid body joints which allow adaption of the curvature of the force transmission element to the curvature of the shaft.

The force transmission element of this known medical tubular shaft instrument comprises poor torque transmission capabilities since the diameter decreased regions of the force transmission element have no significant torsional rigidity. In addition, the diameter decreased regions of the force transmission element are susceptible to material fatigue leading to fractures and cracks within the force transmission element. Furthermore, the force transmission element cannot be used in the curved instruments with a tight bend due to its limited flexibility.

SUMMARY OF THE INVENTION

It is an object of the present invention to improve a medical tubular shaft instrument of the type mentioned at the outset such, that significant forces even along curved sections of the shaft and along in principle arbitrary shaped and oriented shaft curvatures can be transmitted without the disadvantages mentioned afore.

According to an aspect, a medical tubular shaft instrument is provided, comprising a tubular shaft having a distal end, a proximal end, and defining a longitudinal direction, the shaft having a shaft section arranged between the distal end and the proximal end of the shaft and having a curvature and an inner surface, a handle arranged at the proximal end of the shaft, a movable working part arranged at the distal end of the shaft, a force transmission element extending through the shaft and being movable in the longitudinal direction of the shaft, the force transmission element operatively connecting the handle and the working part, the force transmission element having a force transmission element section arranged within the shaft section having the curvature, the force transmission element section being guided on the inner surface of the shaft section, the force transmission element section further having a plurality of interconnected single elements arranged one after the other along the longitudinal direction of the shaft, the single elements being pairwise connected through a hinged joint, each hinged joint having a pin, each of the pins oriented substantially perpendicular relative to the longitudinal direction of the shaft and defining a rotation axis of a pair of the interconnected single elements.

An advantage of the force transmission element of the medical tubular shaft instrument according to the invention is, that it comprises single elements being pairwise connected by means of pins, wherein pairs of single elements form hinged joints. Thus, the pins ensure a form-locking connection between the single elements being arranged next to each other. This form-locking connection ensures a high degree of axial rigidity which is important to transmit push and/or pull forces.

In addition, the susceptibility against lateral forces which can affect single elements is suppressed along the rotation axes of the single elements since in this direction no motion of the single elements can occur. However, the rotational degree of freedom the single elements have allows to adapt the force transmission element to the given shaft curvature and even to transmit high push and/or pull forces.

In an optional refinement the rotation axis defined by at least one of the pins is orientated non-parallel to the rotation axes defined by the other pins.

Furthermore, the rotation axes defined by pins of adjacent single elements are oriented non-parallel relative to each other.

The arrangement mentioned afore has the advantage, that it allows to adapt the curvature of the force transmission element to the curvature of the shaft in more than one plane. This arrangement of the pins and its specific orientations further allows the force transmission element to follow changing orientations of shaft curvatures, for example if the shaft is semi-flexible or semi-rigid and, thus, the curvature of the shaft can be changed.

In a further preferred refinement the rotation axes defined by pins of adjacent single elements are oriented at least approximately perpendicular to each other.

Orienting the rotation axes of the pins which are arranged next to each other as mentioned afore, leads to a cardanic configuration of adjacent hinged joints of single elements. The degrees of freedom of the force transmission element are thereby further increased, allowing for in principle arbitrary shaped curvatures and orientations of the force transmission element. The cardanic arrangement of alternating orientations of the pins connecting the single elements ensures a playless force transmission of push and/or pull forces in the longitudinal direction of the shaft and the ability of the force transmission element to follow in principle arbitrary shaped and orientated curvatures of the shaft.

In a further preferred refinement of the invention the single elements are shaped in forms of cylinders and being bevelled at at least one of their longitudinal end faces.

The cylindrical shape of the single elements is well adapted to a circular cross-section of the shaft, which is common for medical instrument shafts. Thus, the single elements are circumferentially guided along the inner surface of the shaft. In addition, the cylindrical shape of the single elements also allows to transmit torques via the force transmission element, because the single elements of the force transmission element can be rotatable within the shaft about the longitudinal direction thereof. The bevelled end faces provide sufficient space for the pivoting movements of the single elements about their rotation axes in two opposite directions. The angle of the slope of the end faces is one parameter to adapt the curvature of the force transmission element to the curvature of the shaft.

Furthermore, smooth outer surfaces of the single elements and smooth inner surface of the shaft are preferred to reduce frictional wear of the force transmission element and/or the shaft.

In a further preferred refinement of the invention the cylinders comprise outer surfaces being in circumferential contact with the inner surface of the shaft for guiding the force transmission element.

The guidance of the force transmission element within the shaft ensures that the force transmission element exactly follows the curvature of the shaft. The guidance of the force transmission element additionally reduces lateral displacements of the force transmission element when transmitting significant push and/or pull forces.

Furthermore, a well-adapted guidance of the force transmission element within the shaft reduces frictional wear of both, the outer surfaces of the single elements and the inner surface of the shaft.

In a further preferred refinement of the invention, two adjacent single elements which are arranged face to face, form at least one wedge-like gap by means of their longitudinal end faces.

The wedge-like gap which is formed between two bevelled end faces of two adjacent single elements ensures the pivotability of two adjacent single elements about their common rotation axis, on the one hand, and, in addition, two bevelled end faces define a limit of the pivoting range which reduces the risk of overstressing the connection between the single elements and the associated risk of damaging the force transmission element.

In a further preferred refinement of the invention, the length of the cylinders and/or the width of the at least one wedge-like gap are adapted to the curvature of the shaft.

Both parameters namely the length of the cylinders and/or the width of the at least one wedge-like gap can be used, independently or in combination, to adapt the "flexibility" of the force transmission element to the curvature of the shaft. The ability to have different parameters to adapt the geometrical conditions of the force transmission element consisting of cylindrical shaped single elements to the curvature and the surface conditions of the inner surface of the shaft is advantageous. A shaft adapted force transmission element eases the handling of the medical instrument and reduces maintenance costs.

In a further preferred refinement of the invention, the single elements comprise at least one eye on both end faces, to bear at least one of the pins.

In a further preferred refinement of the invention, one of the pins engages into at least a first eye of a first single element and at least a second eye of the adjacent single element adjacent to the first single element.

The connection of one pin with at least a first eye of a first single element and with at least a second eye of the adjacent second single element ensures that the pin connects the first single element and the adjacent single element rotatably about their rotation axis and axially fixed along the longitudinal direction of the force transmission element, especially without play.

In addition, this form-locking connection of the pins and the eyes provides a significant torsional and axial rigidity leading to excellent push and/or pull force transmission capabilities as well as excellent torque transmission capabilities.

In a further preferred refinement of the invention, the force transmission element comprises a rigid elongated portion connected to the section comprised of the interconnected single elements.

Combining a rigid section of the force transmission element with a curved section of the force transmission element has the advantage that the section comprised of the single elements can be present in the curved section of the shaft only, while the rigid portion is used in regions where the shaft is straightly elongated. The configuration eases the construction and reduces production costs and additionally ensures an effective force transmission capability via the force transmission element.

Thus, the capability of transmitting push and/or pull forces as well as torques with the force transmission element is maximized by the rigid sections of the force transmission element in the regions where the shaft is straightly elongated and by the hinged sections of the force transmission element in the curved section or sections of the shaft.

In a further preferred refinement of the invention, the force transmission element is rotatable relative to the shaft about the longitudinal direction of the shaft.

The given arrangement of the force transmission element ensures, that also torques can be transmitted through the force transmission element which can be actuated by a rotating device being arranged on the handle. The torque can be transmitted to the working part leading to a rotation of the working part about the longitudinal direction of the shaft. This rotation of the working part can be desired during an operation to bring the jaw parts in the right position for cutting and/or grasping tissue regions within the body cavity of a patient.

Further advantages will become apparent from the following description and the accompanying drawings. It is to be understood that the afore-mentioned features and those to be explained below are not only applicable in the combination given but also in other combinations or in isolation without departing from the scope of the invention.

BRIEF DESCRIPTION OF THE DRAWINGS

Exemplary embodiments of the invention are illustrated in the drawings and will be described hereinafter with reference thereto. In the drawings.

DETAILED DESCRIPTION OF PREFERRED EXEMPLARY EMBODIMENTS

Figure 1:
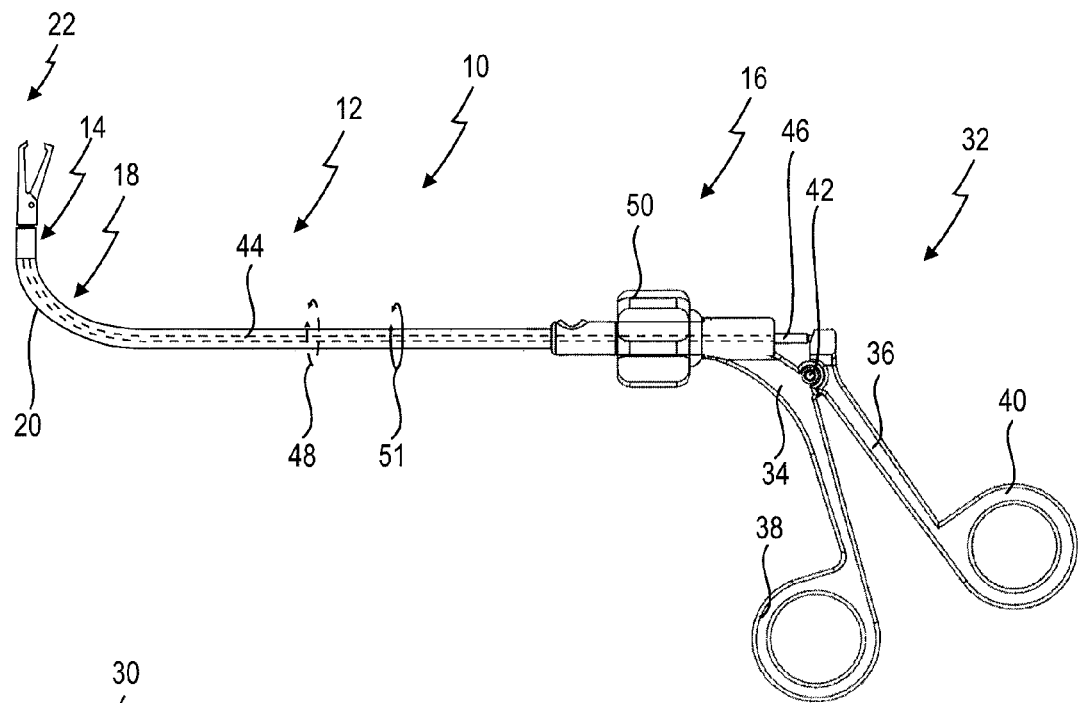
FIG. 1 shows a medical tubular shaft instrument in a side view.

FIG. 1 shows a medical tubular shaft instrument labelled with general reference numeral 10. The medical instrument 10 is configured as a forceps, in particular for use in endoscopic surgery.

Further details of the instrument 10 are shown in FIGS. 2 through 5.

With reference to FIG. 1, the instrument 10 comprises a tubular shaft 12 which has a distal end 14 and a proximal end 16.

The shaft 12 has at least one curved section 18 between the distal end 14 and the proximal end 16 of the shaft 12. In the present embodiment, the curved section 18 has one curvature 20 so that the distal end 14 and the proximal end 16 of the shaft 12 form an angle with one another.

It is to be understood that the curved section 18 could also have a curved section 18 comprising two or more curvatures 20 forming an S-shape or meander shape (not shown).

The curved section 18 may be permanent if the shaft 12 is rigid, wherein the curved section 18 has been shaped when manufacturing the shaft 12.

It is, however, also possible that the shaft is semirigid or semiflexible so that the curved section 18 can be shaped by the user of the instrument by bending the curved section 18 of the shaft 12 into a desired shape.

A working part 22 is arranged at the distal end 14 of the shaft 12. The working part 22 has an immovable working element 24 and a movable working element 26. The working elements 24 and 26 are rotatably connected by a bolt 28 and are configured as jaw parts 30 for grasping and/or cutting tissue, for example. In the embodiment shown in FIG. 1, the medical tubular shaft instrument 10 is a grasping instrument.

A handle 32 is arranged at the proximal end 16 of the shaft 12. The handle has an immovable grip part 34 and a movable grip part 36. The immovable grip part 34 has a finger ring 38 and the movable grip part 36 has a second finger ring 40. The movable grip part 36 is connected with the immovable grip part 34 via a handle joint 42.

The movable grip part 36 is operatively connected with the movable working element 26 via a force transmission element 44 (shown in FIG. 1 by broken lines), wherein the force transmission element 44 extends through the shaft 12 so that only a proximal end portion 46 of the force transmission element 44 can be seen in FIG. 1. The force transmission element 44 is capable to transmit at least push and/or pull forces from the handle 32 to the movable working element 26. Further, the force transmission element 44 must also have a sufficient torsional rigidity to constrain the rotation of the working part 22 about its longitudinal direction. The force transmission element 44 also has a sufficient compressive and/or tensile strength to ensure a sufficient transmission capability of push and/or pull forces from the handle 32 to the movable working element 26.

The force transmission element 44 is rotatable about the longitudinal direction of the shaft 12 as indicated by an arrow 48 in FIG. 1. The force transmission element 44 can be rotatable in both directions over 360°. A rotating device 50 is arranged distally from the immovable grip part 34 for actuating the rotation of the force transmission element 44. The shaft 12 can be rotatable in both directions over 360°, which is indicated by a second arrow 51. The rotating device 50 can be configured to also rotate the shaft 12 independently from the force transmission element 44. The rotating device 50 is configured as a wheel which can be actuated by the index finger while the finger rings 38 and 40 are held with the thumb and the middle finger of the same hand holding the instrument 10.

The force transmission element 44 comprises at least one articulated section 52 being arranged between the distal end 14 and the proximal end 16 of the shaft 12. The section 52 is accommodated within the curved section 18 of the shaft and comprises a plurality of interconnected single elements 54. Further details of the section 52 of the force transmission element 44 and the single elements 54 are shown in FIGS. 2 through 5 and will be described below.

During a medical surgery a distal portion 56 of the shaft 12 is introduced into a body cavity of a patient for grasping and/or cutting tissue (not shown). To this end, the jaw parts 30 and the distal portion 56 of the shaft 12 are introduced into the body cavity to execute the grasping and/or cutting action which are performed by a surgeon.

Depending on the application a surgeon would like to perform, considerably high forces and/or torques need to be transmitted to the jaw parts 30 which are transmitted from the handle 32 and/or the rotating device 50 to the jaw parts for grasping and/or cutting tissue regions within the body cavity.

To transmit the required forces and/or torques from the movable grip part 36 and/or the rotating device 50 to the movable working element 26 even through the curved section 18 of the shaft 12 the section 52 of the force transmission element 44 has a chain of interconnected single elements 54 arranged at least within the curved section 18 of the shaft 12.

As best seen in FIGS. 2 through 5 the chain of interconnected single elements 54 has a distal connector 58 connecting the force transmission element 44 with the jaw parts 30 and a proximal connector 60 connecting the section 52 of single elements 54 with an elongated portion 62. The elongated portion 62 is configured as a rigid monolithic portion of the force transmission element 44 in the embodiment shown and is together with the section 52 at least axially movable with respect to the shaft 12 in order to transfer a movement of the movable grip part 36 into a movement of the movable working element 26 via the chain of interconnected single elements 54 for closing and/or opening the movable jaw parts 30.

Figure 2:
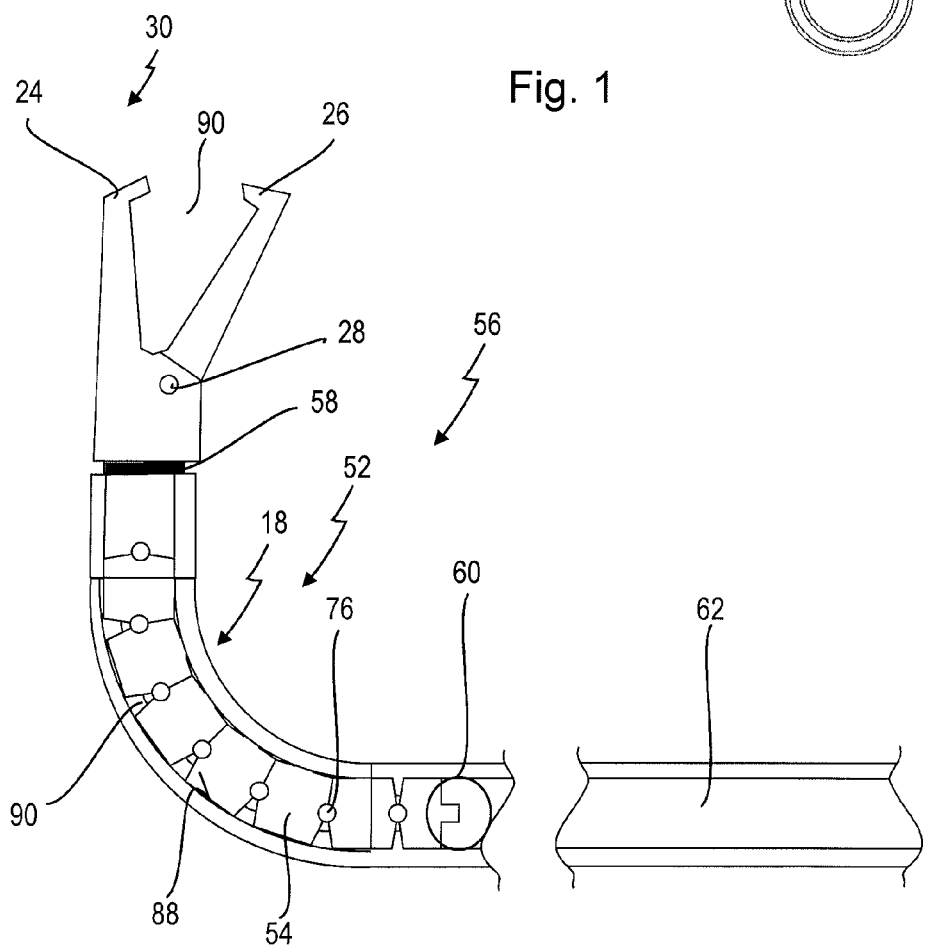
FIG. 2 shows an enlarged view of a curved section of a shaft and a curved section of a force transmission element within the shaft of the medical tubular shaft instrument of FIG. 1.
Figure 5:
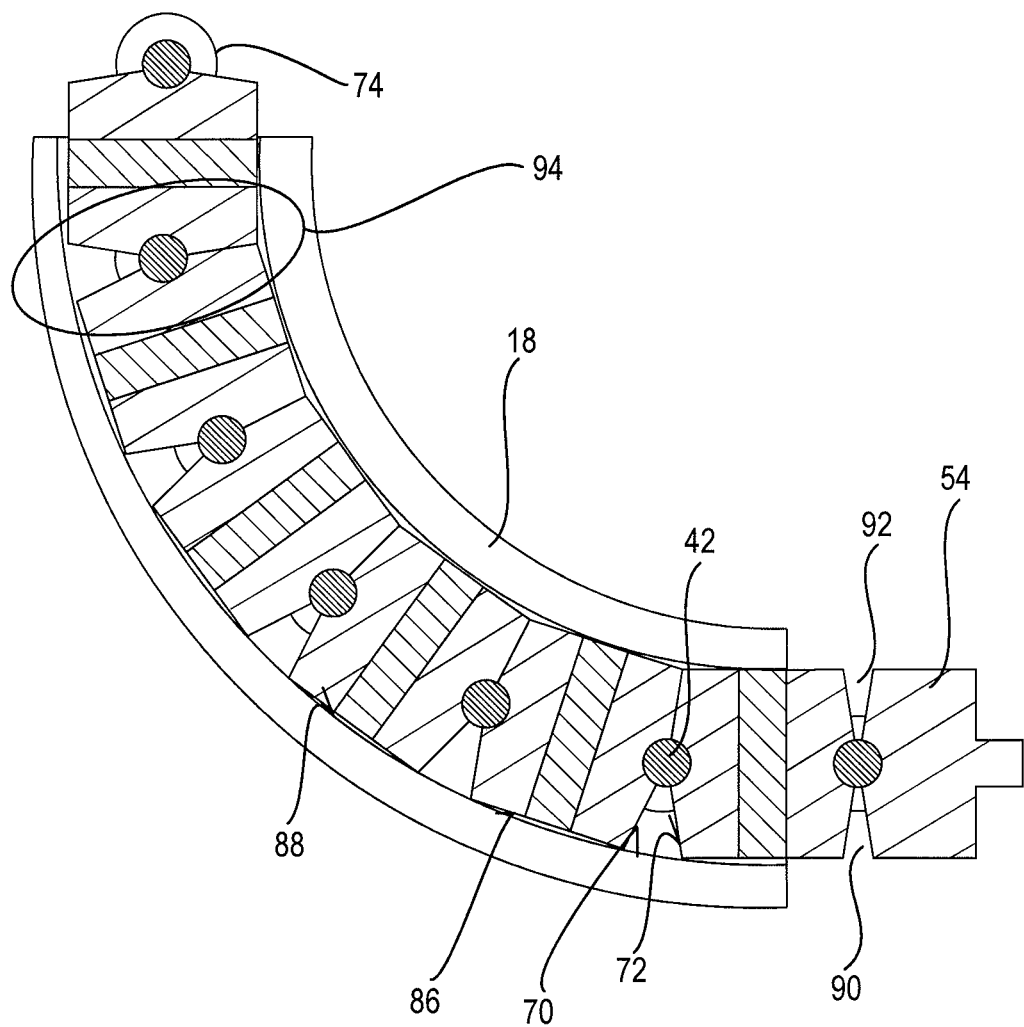
FIG. 5 shows a sectional view of the curved section of the force transmission element of FIG. 4 arranged within the curved section of the shaft.

As best seen in FIG. 2 and FIG. 5, at least the section 52 of interconnected single elements 54 is guided within the curved section 18 of the shaft 12.

The guidance of the force transmission element 44 within the shaft 12 ensures that a movement of the force transmission element 44 follows the curvature 20 of the shaft 12.

Figure 3:
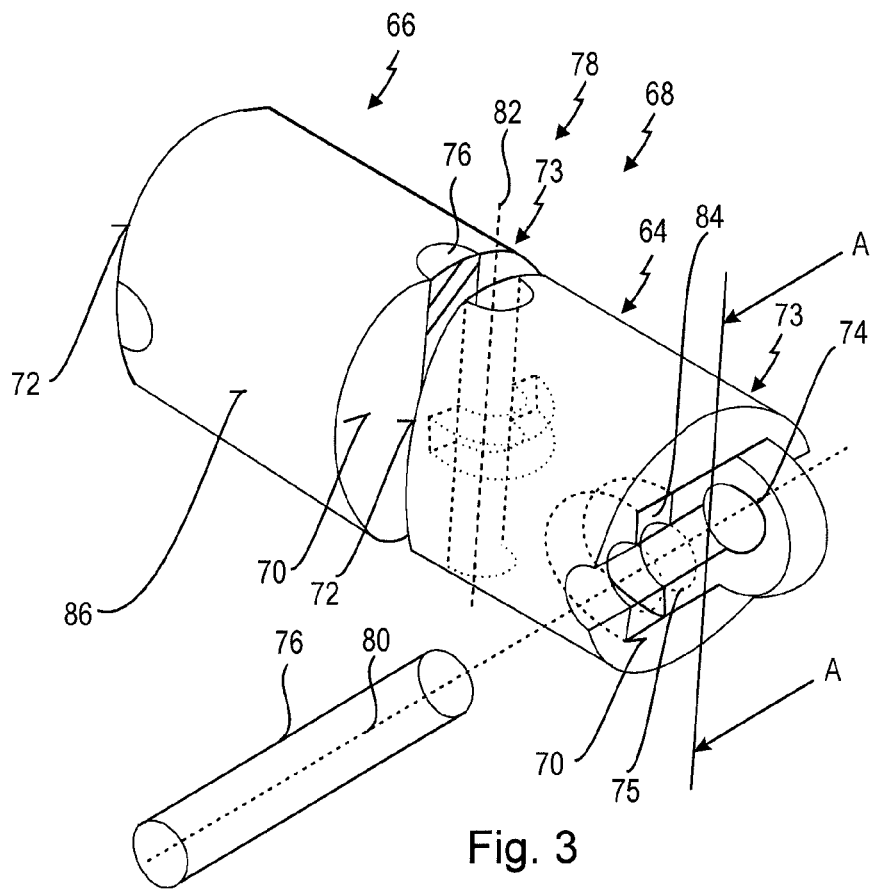
FIG. 3 shows an embodiment of a detail of the force transmission element of FIG. 2 of the medical instrument of FIG. 1 in a perspective view.
Figure 4:
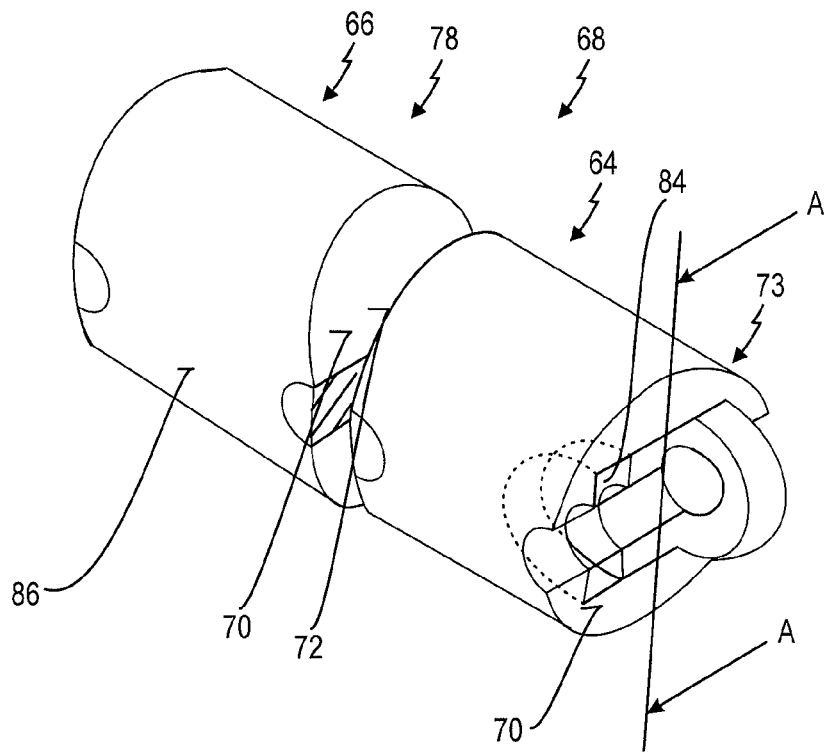
FIG. 4 shows another embodiment of a detail of a force transmission element for use in the medical instrument of FIG. 1 in a perspective view.

As best seen in FIG. 3 and FIG. 4 the chain of interconnected single elements 54 is configured of a first single element 64 and an adjacent second single element 66 wherein the second single element 66 is arranged relative to the first single element 64 along the longitudinal direction of the shaft 12. In the embodiments shown in FIG. 3 and FIG. 4 each of the single elements 54 are shaped in forms of cylinders 68 and have a first end face 70 and a second end face 72 while both end faces 70, 72 comprise an eye 73 where a pin 76 engages through.

In addition, the single elements 54 are arranged such, that the second end face 72 of the first single element 64 and the first end face 70 of the adjacent single element 66 comprise a first eye 74 and a second eye 75 which are oriented such, that the pin 76 can be accommodated therein.

Therefore, the pin 76 connects the first single element 64 and the second single element 66 in form of a hinged joint 78, wherein the first and the second single element 64, 66 are rotatably arranged relative to the pin and about the rotation axis 80 defined by the pin 76. While the assembling of the chain of single elements 54 has been exemplary described with respect to a first and a second interconnected single element 64, 66 forming a hinged joint, the chain of single elements 54 is an arrangement of interconnected first and second single elements 64, 66 forming hinged joints which are arranged in series.

In the preferred embodiment shown in FIG. 3, the pins 76 connecting the single elements 54 are oriented such, that at least one rotation axis 82 of the hinged joints 78 is oriented substantially non-parallel to the rotation axes 80 of the other pins 76.

In this preferred embodiment at least one eye 73 arranged on the first end face 70 of a first single element 64 is oriented substantially parallel to a plane A and an adjacent eye 73 which is arranged on the first end face 70 of a second adjacent single element 66 is oriented substantially perpendicular to the plane A.

Thus, the orientation of two eyes 73 arranged at the first end faces 70 of two adjacent single elements 64, 66 are alternately oriented parallel and perpendicular relative to the plane A and to each other. The alternating orientation of the two eyes 73 of adjacent single elements 64, 66 and for a chain of interconnected single elements 54 allow an arrangement of single elements 54 in nearly arbitrary shape and make the arrangement of single elements 54 therefore adaptable to a given shaft 12 and its curvature 20.

It can best be seen in FIG. 3 and FIG. 4 that the first end face 70 and the second end face 72 comprise recesses 84 where the eyes 73 can be rotated in. The recesses 84 accommodate the eyes 73 and guide the eyes 73 by a pivoting movement about the rotation axis 80 defined by the pin 76. A guidance of the eyes 73 within the recesses 84 reduces play between two adjacent single elements 54 causing an increased rigidity of two adjacent single elements 64, 66 in direction parallel to the rotation axis 80 defined by the pins 76.

The cylindrical shaped single elements 54 have an outer surface 86 being at least partially in contact with an inner surface 88 of the shaft 12. Hence, at least the curved section 52 of the force transmission element 44 is guided within the shaft 12 along the inner surface 88 of the shaft. The bevelled end faces 70, 72 of a first single element 64 and an adjacent second single element 66 form at least one wedge-like gap 90.

In a preferred embodiment the width of a first wedge-like gap 90 has the same width as a second wedge-like gap 92 which is oriented face to face relative to the eyes 74, 75 and the pin 76 connecting the first single element 64 and the adjacent second single element 66.

As best seen in FIG. 5, the curved section 52 of the force transmission element 44 can be adapted to the curved section 18 of the shaft 12 by adapting the length of the single elements 44 and/or by adapting the width of the wedge-like gaps 90, 92 between the first end face 70 and the second end face 72 of two adjacent single elements 64, 66.

It is further preferred to combine both, adapting parameters given by the width of the wedge-like gaps 90 and the length of the cylinders 68 of the single elements 44 to achieve best fitting conditions for the curved section 52 of the force transmission element 44 within the given curvature 18 of the shaft 12.

In FIG. 4 an embodiment is shown, where the adjacent eyes 73 and pins 76 can also be oriented parallel to each other and perpendicular to the plane A. This arrangement, where the pins 76 which are arranged along the section 52 of interconnected single elements 54 are oriented parallel to each other, can be used to transmit push and/or pull forces along a well-defined curvature 18 of the shaft 12 in a single plane defined by the plane of the curvature 18.

The connection between a first single element 64 and a second single element 66 by accommodating a pin 76 in the corresponding eyes 74, 75 allow to implement a nearly form-locking playless connection 94 between the pin 76 and the corresponding eyes 74, 75. The form-locking connection 94 between the pins 76 and the eyes 74, 75 has an axial strength which is advantageous to transmit even significant forces from the movable grip part 36 to the movable working element 26. In the present embodiment, only one force transmission element 44 is used to transmit push and/or pull forces as well as torques from the handle 32 and the rotating device 50 to the jaw parts 30.

During a medical surgery the jaw parts 30 are introduced into a body cavity of a patient for grasping and/or cutting tissue. For this, a gap 96 between the movable grip part 36 and the immovable grip part 34 can be increased by transmitting pushing forces via the force transmission element and decreased by transmitting pulling forces or vice versa.

In known instruments, the transmission of significant forces via the force transmission element can cause a deformation of the section of the force transmission element which is guided within the curved section of the shaft. The form-locking connections between the single elements 54 and the guidance of the cylindrical shaped single elements 54 along the inner surface 88 of the shaft 12 decreases the described deformation effect significantly. These effects are also known as buckling, flexing and flipping of the force transmission element between two positions.

As best seen in FIG. 5, the curved section 52 of the force transmission element 44 can be adapted to the curved section 18 of the shaft 12 by adapting the length of the single elements 54 and/or by adapting the width of the wedge-like gaps 90, 92 between the first end face 70 and the second end face 72 of two adjacent single elements 64, 66.

It is further preferred to combine both, adapting parameters given by the width of the wedge-like gaps 90 and the length of the cylinders 68 of the single elements 54 to achieve best fitting conditions for the curved section 52 of the force transmission element 44 within the given curvature 18 of the shaft 12.

When rotating the shaft 12 relative to the force transmission element 44, the force transmission element 44 is also capable to follow the curvature 20 in each rotational orientation of the shaft 12. Thus, the force transmission element 44 allows to follow the curvature 20 of the shaft 12 in arbitrary orientations of the curved section 18 of the shaft 12.

It is easy to understand, that the cardanic form-locking connection 94 between the single elements 54 ensures a transmission of push and/or pull forces as well as a torque transmission to the jaw parts 30 via the force transmission element 44 along the curvature 20 for each orientation of the shaft 12.

Further, the force transmission element 44 can also be realized by an arrangement of eyes 73 and pins 76 having an orientation different from the ones described above. Especially the configuration described in FIG. 4, where adjacent eyes 73 and pins 76 are orientated parallel to each other yields to a simple solution for transmitting forces when a reduced degree of freedom given by the curvature 20 of the shaft 12 is acceptable and no torques have to be transmitted from the rotating device 50 to the jaw parts 30 through the curved section 52 of the force transmission element 44, and if no shaft rotation 12 is needed.

Although the invention has been described with reference to a particular arrangement of parts, features and the like, these are not intended to exhaust all possible arrangement of features and indeed many other modifications and variations will be ascertainable to those of skilled in the art.

What is claimed is:

1. A medical tubular shaft instrument, comprising
   a tubular shaft having a distal end and a proximal end, the shaft defining a longitudinal direction, the shaft having a shaft section arranged between the distal end and the proximal end of the shaft, the shaft section having a curvature and an inner surface,
   a handle arranged at the proximal end of the shaft, the handle having a movable grip part,
   a working part arranged at the distal end of the shaft, the working part having jaws to at least grasp or cut tissue,
   a force transmission element extending through the shaft, the force transmission element having a force transmission element section arranged within the shaft section having the curvature, the force transmission element section being guided on the inner surface of the shaft section, the force transmission element section having
      a plurality of interconnected single elements arranged one after the other along the longitudinal direction of the shaft, the single elements being pairwise connected through a hinged joint, each hinged joint having a pin, each of the pins oriented substantially perpendicular relative to the longitudinal direction of the shaft and defining a rotation axis of a pair of the interconnected single elements,
   the plurality of interconnected single elements operatively connecting the handle and the working part to transmit at least one of a pull force and a push force in the longitudinal direction of the shaft from the handle through the curvature of the shaft section to the working part, such that movement of the movable grip part transfers into movement of the plurality of interconnected single elements along the curvature and into relative movement of the jaws.

2. The instrument of claim 1, wherein the rotation axis defined by at least one of the pins is oriented non-parallel to the rotation axes defined by the other pins.

3. The instrument of claim 1, wherein the rotation axes defined by the pins of adjacent single elements are oriented substantially non-parallel to each other.

4. The instrument of claim 1, wherein the rotation axes defined by the pins of adjacent single elements are oriented at least approximately perpendicular to each other.

5. The instrument of claim 1, wherein the single elements are shaped in forms of cylinders, at least one longitudinal end face of the single elements being bevelled.

6. The instrument of claim 5, wherein the cylinders have outer surfaces being in circumferential contact with the inner surface of the shaft section for guiding the force transmission element.

7. The instrument of claim 5, wherein two adjacent single elements which are arranged face to face, form at least one wedge-like gap between the two adjacent single elements.

8. The instrument of claim 5, wherein a length of each of the cylinders is adapted to the curvature of the shaft.

9. The instrument of claim 7, wherein a size of the at least one wedge-like gap is adapted to the curvature of the shaft.

10. The instrument of claim 1, wherein the single elements having two opposite end faces, the single elements comprise at least one eye on each of the two end faces to bear at least one of the pins.

11. The instrument of claim 1, wherein one of the pins engages into at least a first eye of a first single element and at least a second eye of a second single element adjacent to the first single element.

12. The instrument of claim 1, wherein the force transmission element comprises a rigid elongated portion connected to the force transmission element section having the interconnected single elements.

13. The instrument of claim 1, wherein the force transmission element is rotatable relative to the shaft about the longitudinal direction of the shaft.

14. A medical tubular shaft instrument, comprising
   a tubular shaft having a distal end and a proximal end, the shaft defining a longitudinal direction, the shaft having a shaft section arranged between the distal end and the proximal end of the shaft, the shaft section having a curvature and an inner surface,
   a handle arranged at the proximal end of the shaft, the handle having a movable grip part,
   a movable working part arranged at the distal end of the shaft,
   a force transmission element extending through the shaft and being movable in the longitudinal direction of the shaft, the force transmission element having a force transmission element section arranged within the shaft section having the curvature, the force transmission element section being guided on the inner surface of the shaft section, the force transmission element section having a plurality of interconnected single elements arranged one after the other along the longitudinal direction of the shaft, the single elements being pairwise connected through a hinged joint, each hinged joint having a pin, each of the pins oriented substantially perpendicular relative to the longitudinal direction of the shaft and defining a rotation axis of a pair of the interconnected single elements, the plurality of interconnected single elements operatively connecting the handle and the working part to transmit at least one of a pull force and a push force from the handle through the curvature of the shaft section to the working part, in order to transfer movement of the movable grip part into relative movement of components of the working part.

* * * * *